Figure 1A:
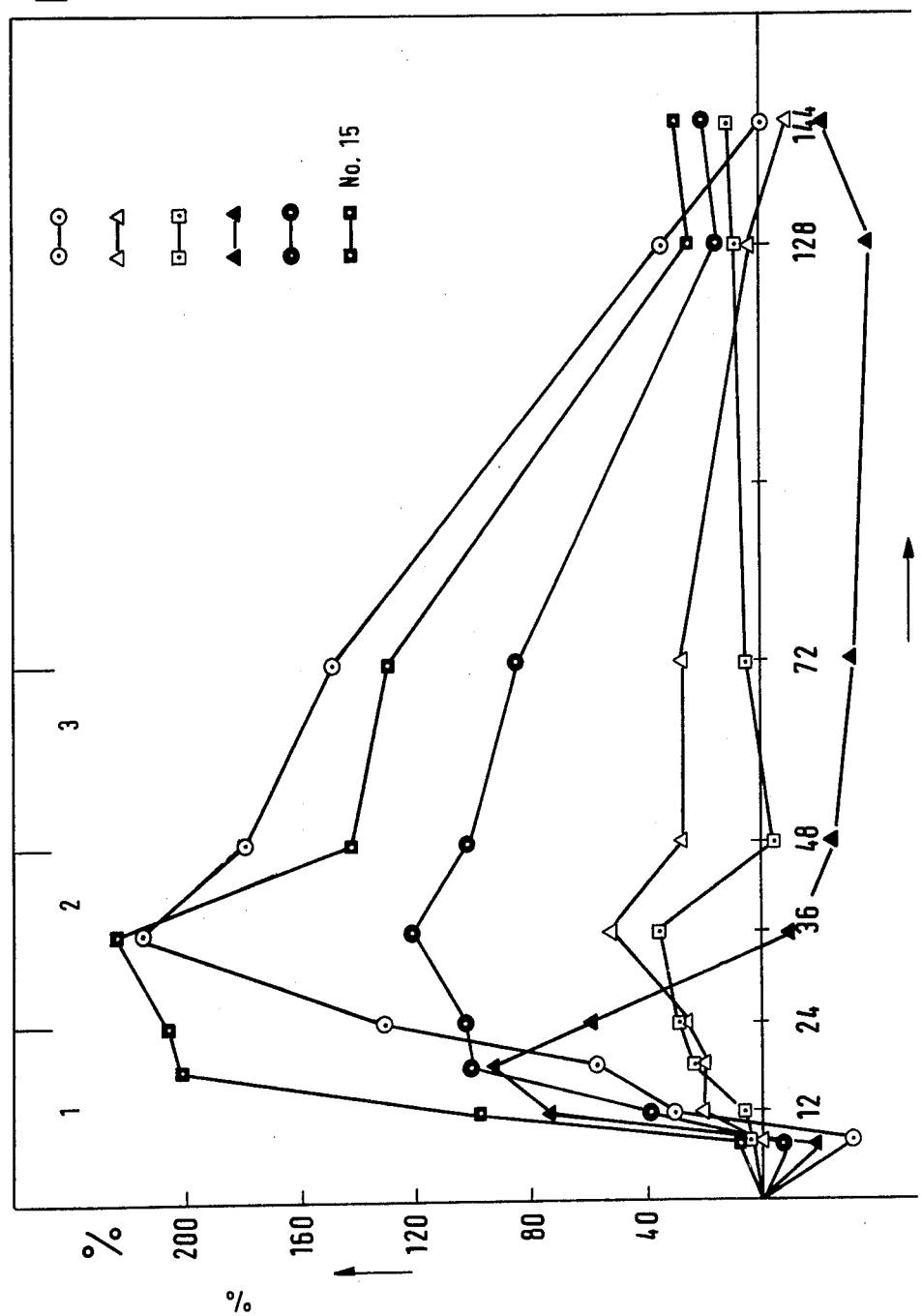

United States Patent [19]

Ruhenstroth-Bauer et al.

[11] 4,215,109
[45] Jul. 29, 1980

[54] MEDICAMENTS FOR THE SUPPRESSION OF PATHOLOGICAL PROCESSES

[75] Inventors: Gerhard Ruhenstroth-Bauer, Gräfelfing; Reiner Scherer, Munich, both of Fed. Rep. of Germany

[73] Assignee: Max-Planck-Gesellschaft zur Forderung der Wissenschaften e.V., Göttingen, Fed. Rep. of Germany

[21] Appl. No.: 906,442

[22] Filed: May 17, 1978

[30] Foreign Application Priority Data

May 20, 1977 [DE] Fed. Rep. of Germany ....... 2722769
Nov. 15, 1977 [DE] Fed. Rep. of Germany ....... 2750920

[51] Int. Cl.$^2$ .............................................. A61K 37/00
[52] U.S. Cl. ....................................................... 424/177
[58] Field of Search ........................................ 424/177

[56] References Cited

U.S. PATENT DOCUMENTS

| | | | |
|---|---|---|---|
| 2,847,348 | 8/1958 | Singher et al. | 424/177 |
| 2,847,349 | 8/1958 | Singher et al. | 424/177 |
| 3,466,368 | 9/1969 | Selo et al. | 424/177 |
| 3,664,994 | 5/1972 | Perper | 424/177 |
| 3,717,708 | 2/1973 | Wada et al. | 424/177 |
| 3,763,135 | 10/1973 | Shanbrom et al. | 424/177 |
| 3,808,189 | 4/1974 | Breuer | 424/177 |
| 3,893,990 | 7/1975 | Fekete et al. | 424/177 |
| 3,893,991 | 7/1975 | Fekete et al. | 424/177 |
| 3,916,026 | 10/1975 | Stephan | 424/177 |
| 3,973,001 | 8/1976 | Jaeger et al. | 424/177 |
| 3,973,002 | 8/1976 | Hagan et al. | 424/177 |
| 4,073,886 | 2/1978 | Kehm | 424/177 |
| 4,081,432 | 3/1978 | Delente et al. | 424/177 |
| 4,087,415 | 5/1978 | Bick et al. | 424/177 |
| 4,093,606 | 6/1978 | Coval | 424/177 |

FOREIGN PATENT DOCUMENTS

| | | | |
|---|---|---|---|
| 2500076 | 1/1975 | Fed. Rep. of Germany | 424/177 |
| 4617152 | 2/1969 | Japan | 424/177 |
| 5176418 | 12/1974 | Japan | 424/177 |
| 1222449 | 11/1968 | United Kingdom | 424/177 |

OTHER PUBLICATIONS

Clemmensen et al., Fibrinogen-Antigenic Material in Arthritis 92, 1978, 678–689.
R. Scherer et al., Naturwissenschaften 64, 471–478, 1977.
J. H. Lewis, PSEBM, vol. 116, 1964 pp. 120–122.
Voss, Hoppe-Seyler's, Z. Physiol. Chem. Bd., 348s, 1172–1178, 1967.

*Primary Examiner*—Delbert R. Phillips
*Attorney, Agent, or Firm*—Peter K. Kontler

[57] ABSTRACT

The increase in concentration of one or several plasma-proteins in the blood is specific for various pathological processes, especially inflammations. A medicament which in a typical way, exactly contains increasingly available plasma-proteins for a pathological process, attenuates the progress of the pathological process, as by this means, the defence system of the body itself is strengthened, which reacts in a specific way on such pathological processes, with the increased formation of one or several plasma-proteins specific for this. This effect is especially demonstrated in regard to Fibrinogen. It demonstrates further that the effect of the Fibrinogen is thereupon to be traced back in that, in regard to reaction with Thrombin at the point of the inflammation, the fibrinopeptides A and B are formed.

4 Claims, 13 Drawing Figures

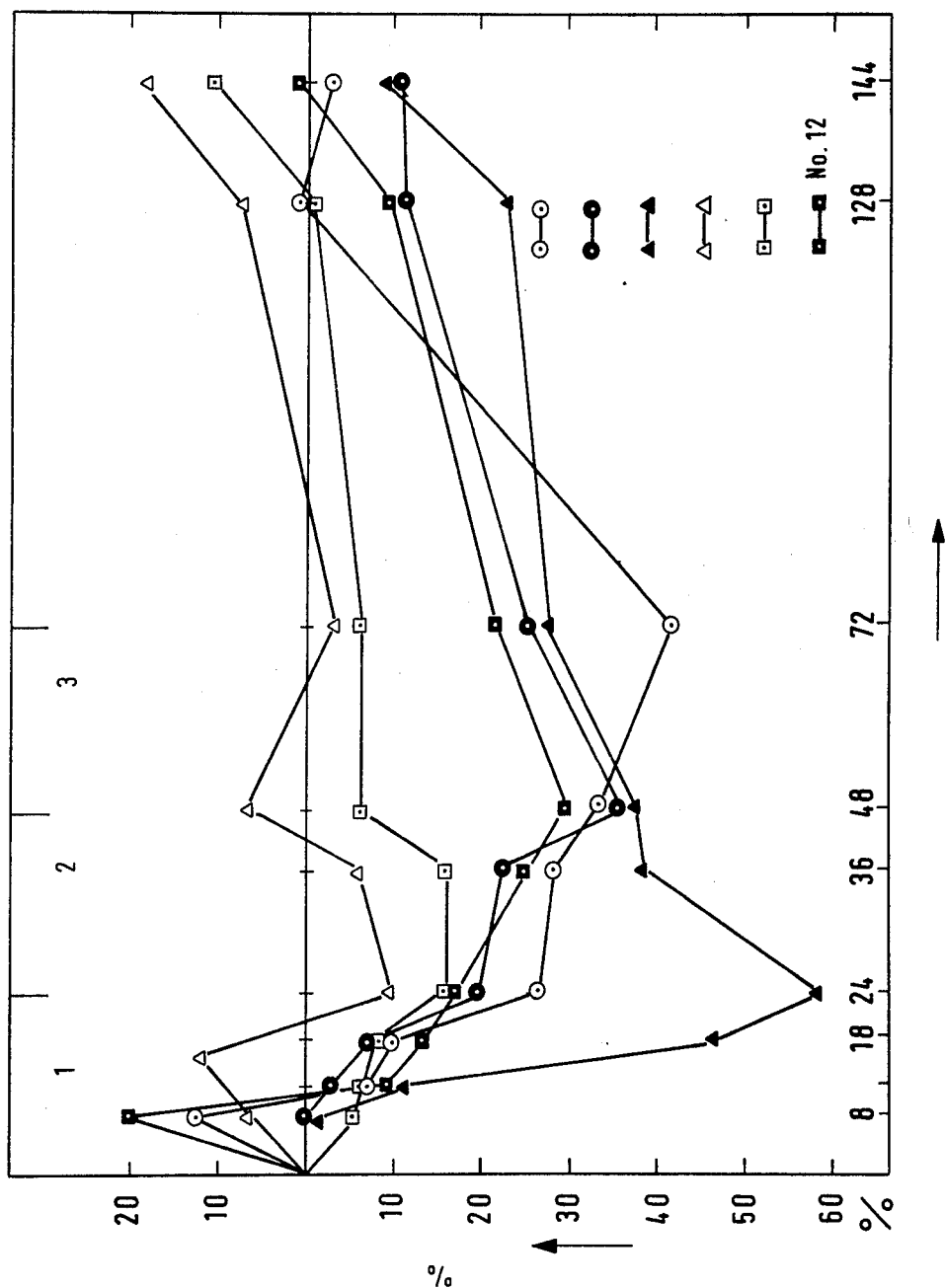

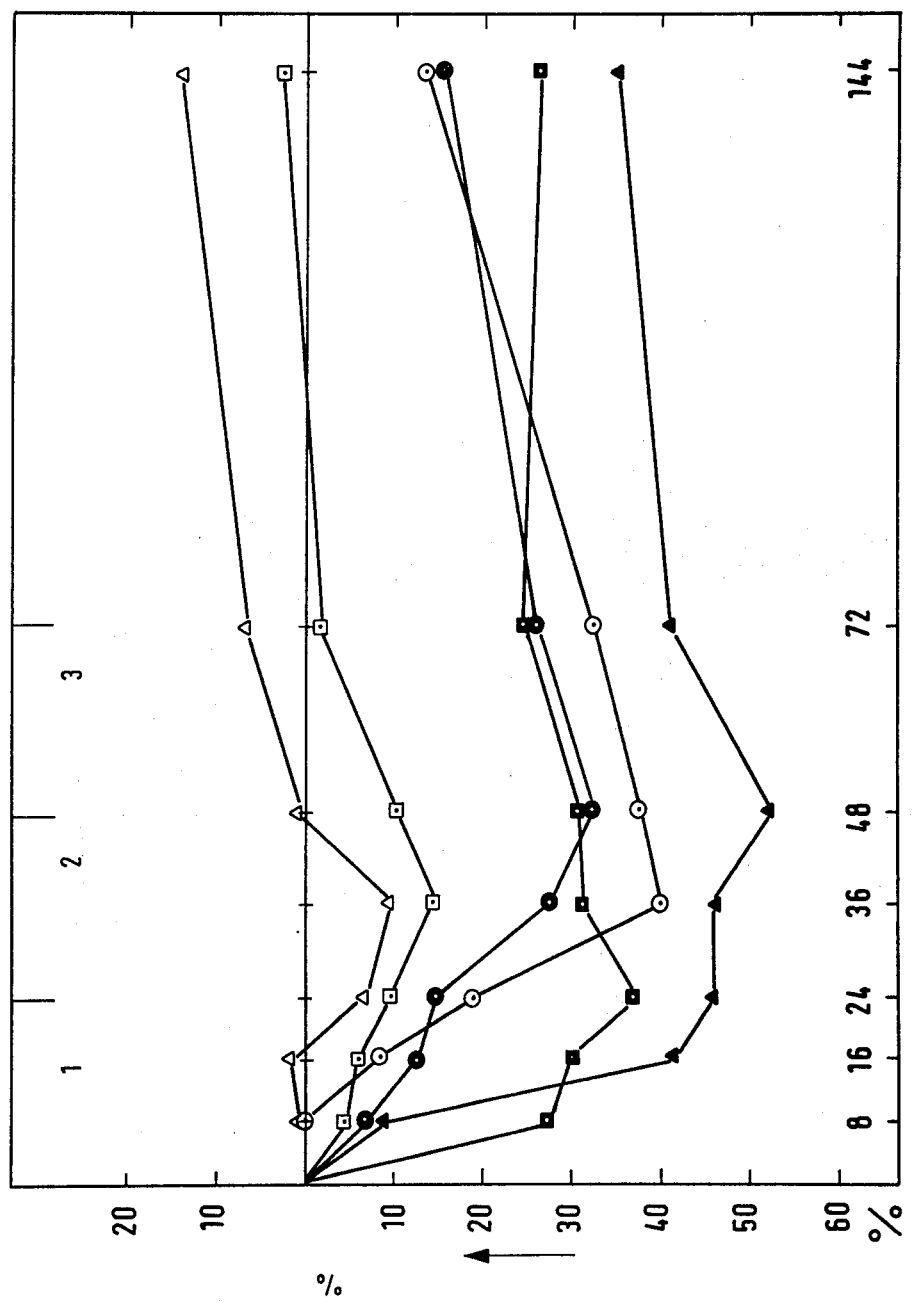

MEDICAMENTS FOR THE SUPPRESSION OF PATHOLOGICAL PROCESSES

The invention concerns a medicament for the prevention and/or attenuation of pathological processes. These pathological processes, especially inflammations, are defined in that they are accompanied by an alteration of the concentration of individual or multiple plasma proteins contained in the serum of the blood, respectively lead to such an alteration.

It is known that most inflammations are accompanied by an increase of the speed of blood corpuscle reduction (BKS). It is further known that the increasing of the BKS speed on the increase of the so-called agglomerine (reduction-acceleration) is to be traced back and that it is thus preponderantly a question of constituents of the blood plasma, especially of the plasma proteins. Thus it has been established that the alteration in the concentration of an individual or several plasma proteins for defined inflammations, in general: is specific for pathological processes, i.e. that definite inflammations result in specific alterations in the concentration of several plasma proteins. Thus, for various pathological processes, specific "plasma-protein-profiles" (PPP) are able to be determined. These realisations led to the achievement of new differential-diagnostic methods, especially in the field of human medicine in regard to hepatitic, nephritic and other forms of illness (compare Scherer, Morarescu, Ruhenstroth-Bauer, Clinical Weekly Magazine 53 (1975), P.265–273; Märki, H. H. German Med. J. 23 (1972), P.217; Boltax A. J., Amer. J. Med. 20, 418 (1956); Hallen, J. Laurell, C. B., Scand. J. Clin. Lab. Invest. 29, Suppl. 124, 97 (1972); Ohlenschläger, G., Berger, I., G. I. T. Fachz. Lab. 18, 1124 (1974); Clarke, H. G. M., Freeman, T., Pryse-Philips, W. E. M., Clin. Sci, 40,337 (1971); Johansson, B. G. et al., Scand. J. Clin. Lab. Invest. 29, Suppl. 124, 117 (1972); Braun, H. J. German Medical Journal 23, (1972), P.227; J. S. Selecta 41 (1974), P. 3574; Kindmark, C. O. et al., Scand. J. Clin. Lab. Invest. 29, Suppl. 124, 105 (1972); Ruhenstroth-Bauer, G., Monthly Course Medical Further Education (Monatskurse ärztl. Fortbildung) 7(1976); Scherer, Medicine in our Time 1, 33 (1977). Acutely inflammatory PPP alterations can occur with people, after irritations such as bacterial infarctions (e.g. erysipelas or gram-negative sepsis) or after uncomplicated surgical operations. The heart muscle necrosis after an infarction also works as a local inflammatory stimulus which leads to a characteristic alteration of the plasma protein composition specified as reaction of the acute phase, and to an acceleration of the BKS (blood corpuscle reduction).

It is the task of the invention to produce a medicament which is suitable for the suppression of all pathological processes such as present themselves by an alteration of the plasma protein profile.

Figure 2A:
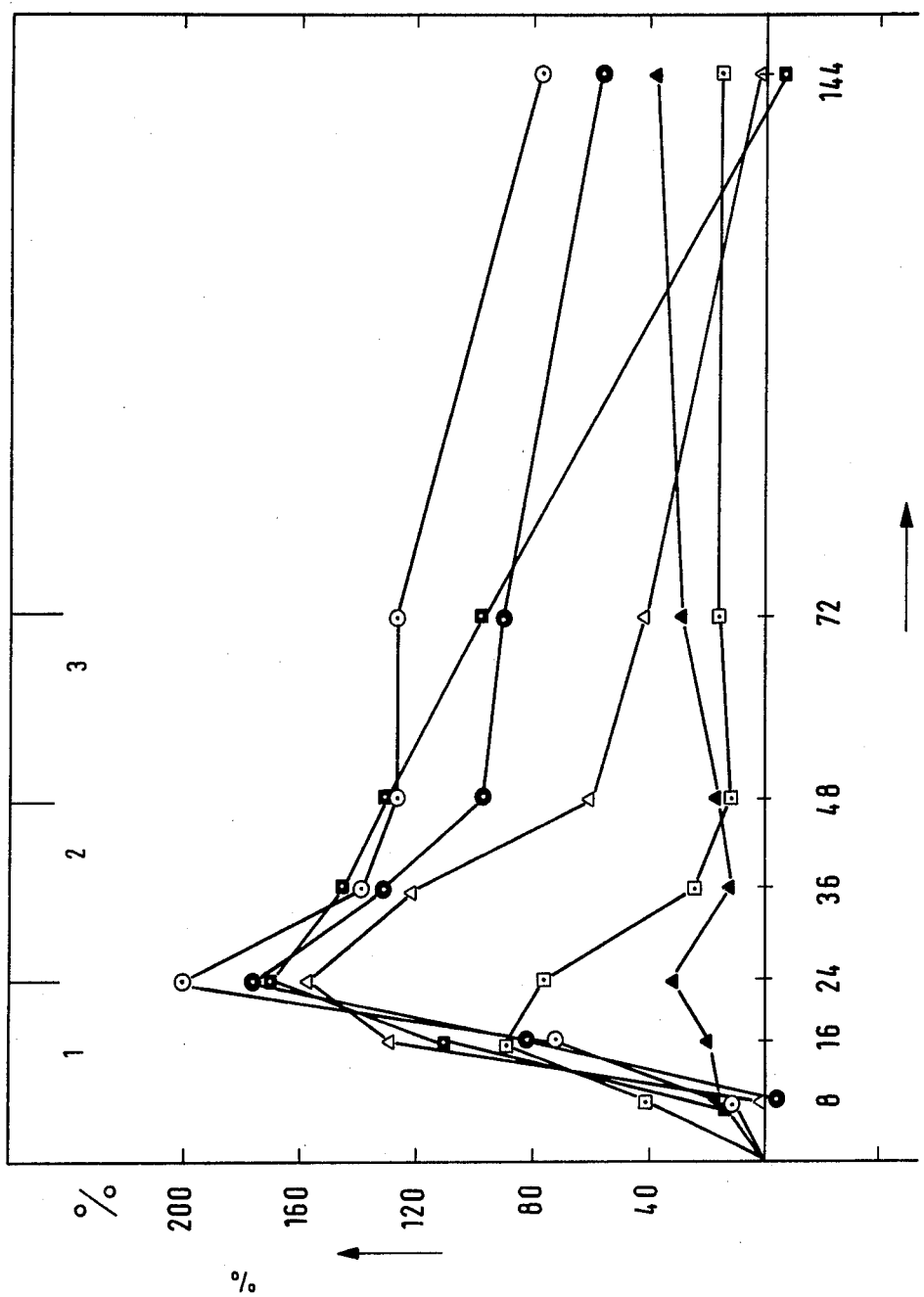
Figure 3A:
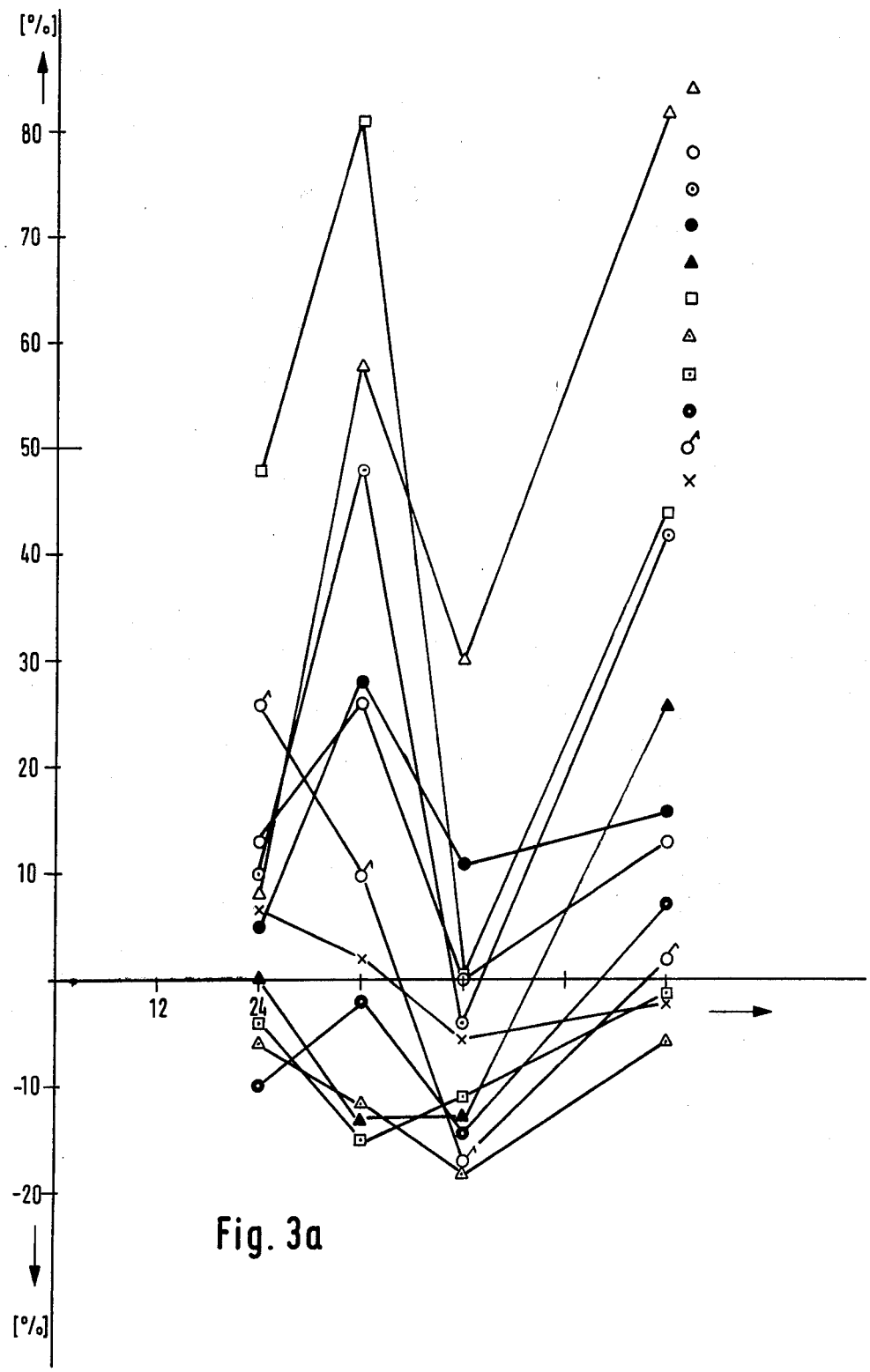
Figure 3B:
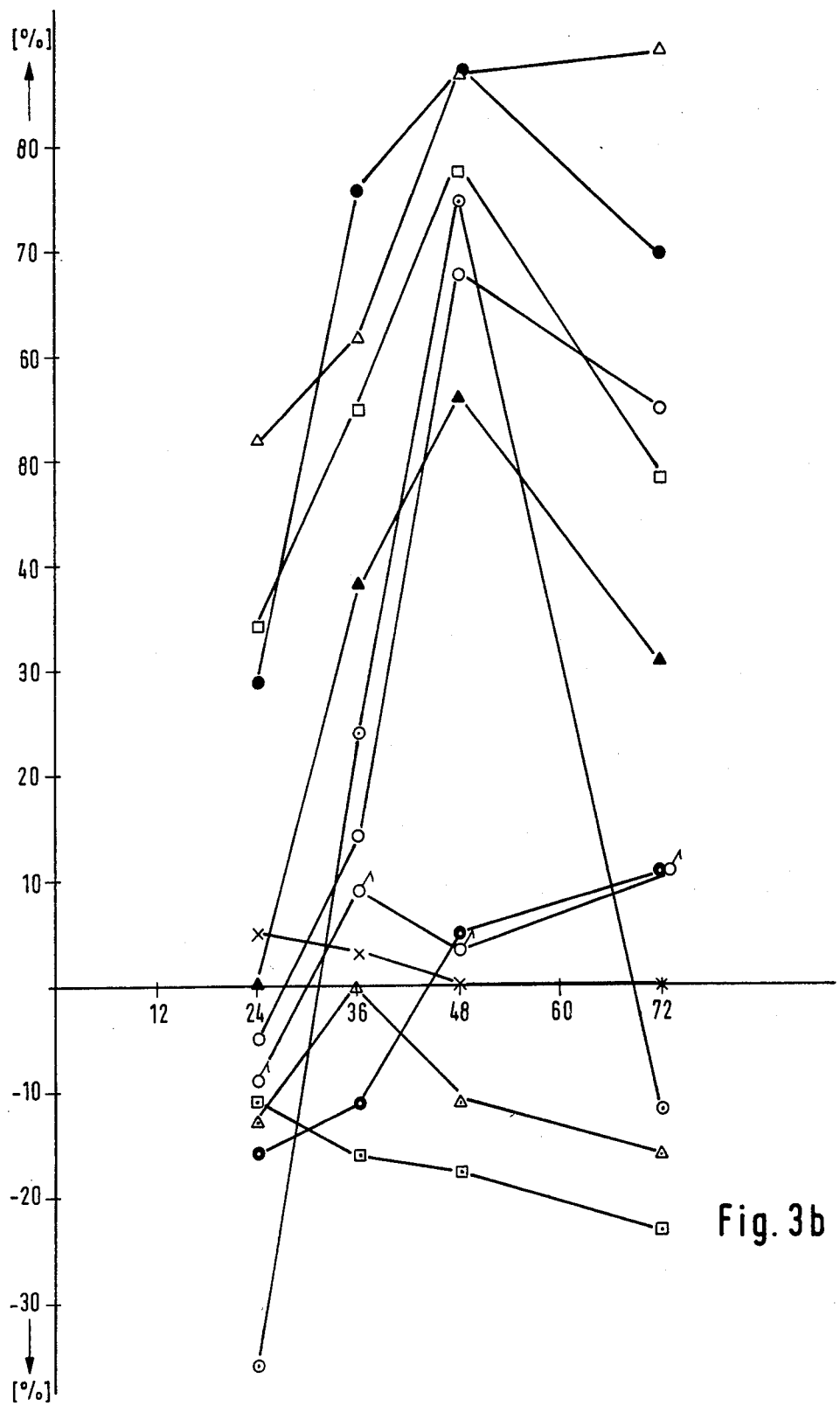
Figure 4:
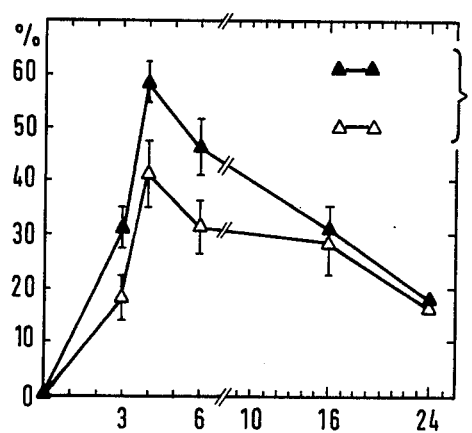
Figure 5A:
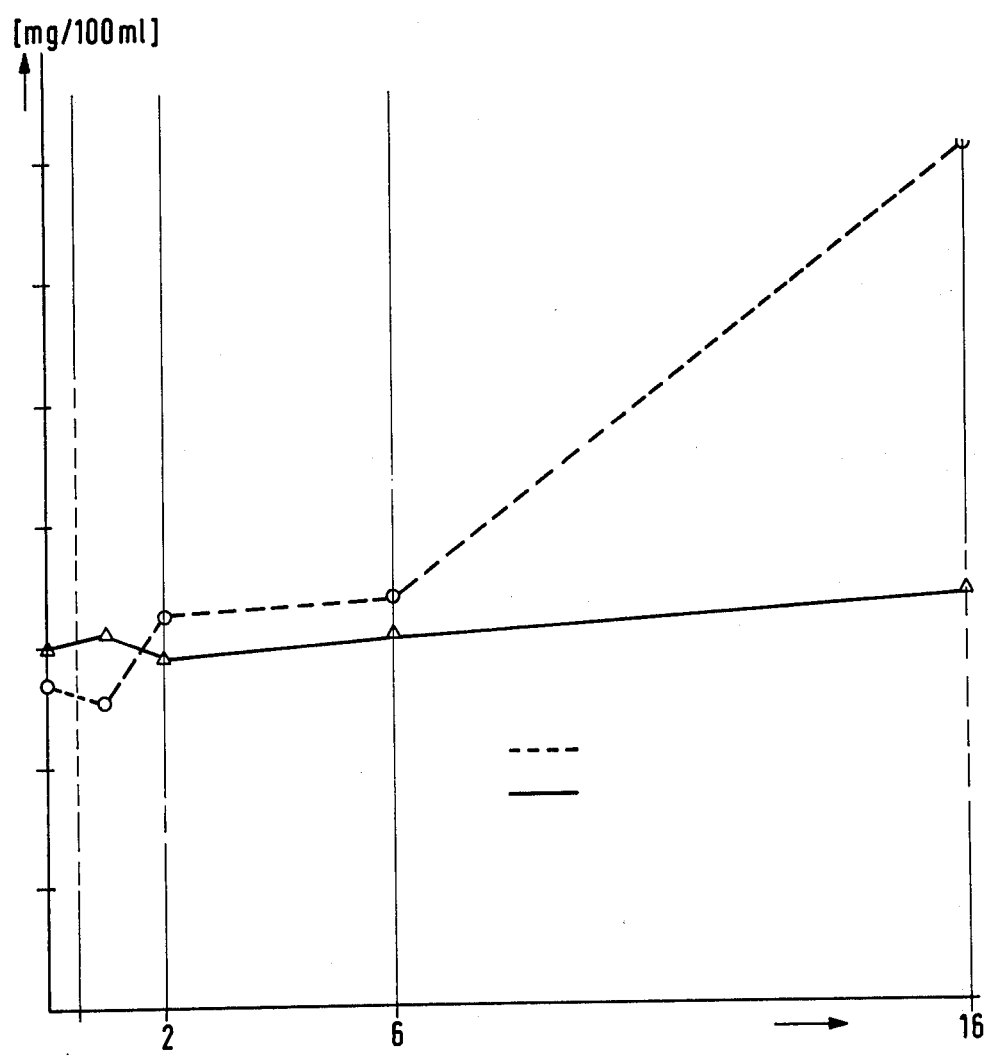
Figure 5B:
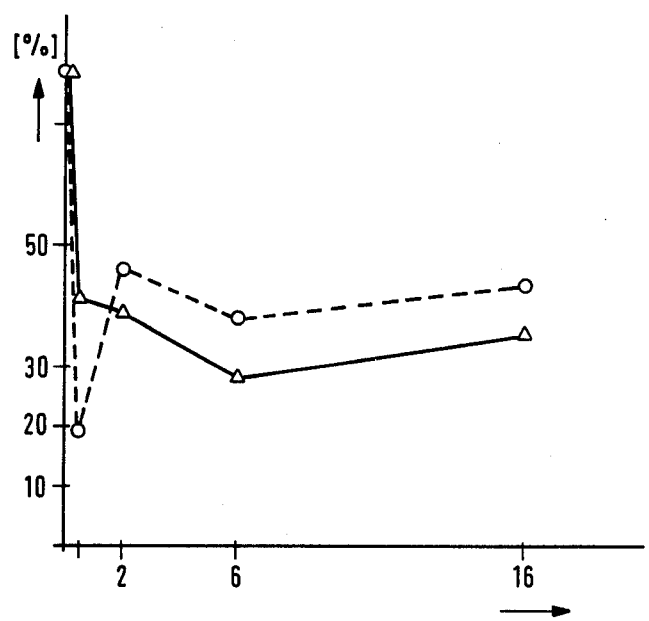
Figure 5C:
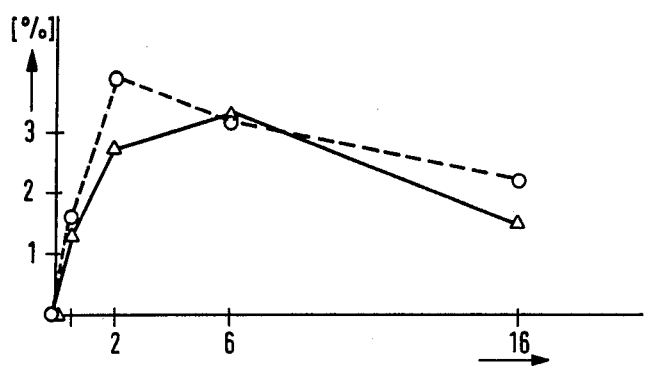
Figure 6A:
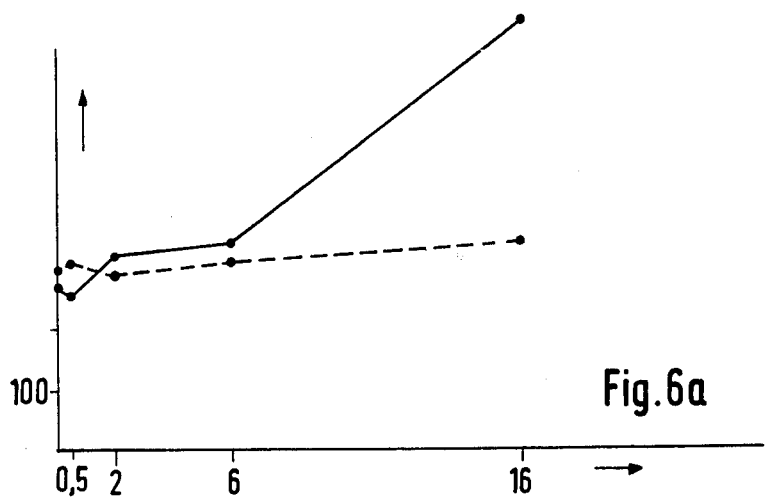
Figure 6B:
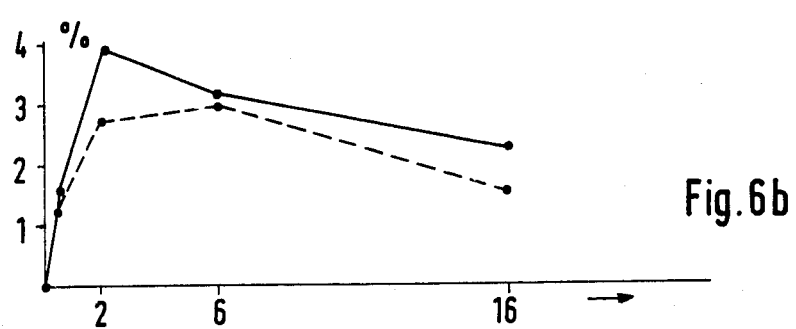
Figure 6C:
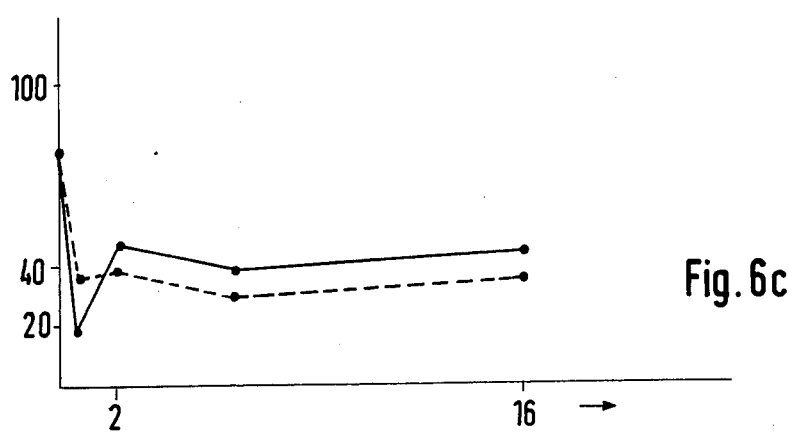

Examples of operation of the invention and its advantageous further developments are described in the following, with the aid of the attached drawings and tables. They describe:

FIGS. 1a, b: the alteration in percentage of the concentration of 12 plasma-proteins in rat serum dependent upon the time after artificial production of an inflammation by intraperitoneal injection of Lipid A;

FIGS. 2a, b: the alteration in percentage of the concentration of 12-plasma-proteins in rat serum dependent on the time after production of an inflammation by sub-plantary injection of Carrageenan in a hind paw;

FIG. 3a, b: The amplification, respectively suppression of the periodic alteration of the concentration of 11 plasma-proteins by injection of Lipid A (FIG. 3a) respectively Carrageenan (FIG. 3b) and at times, simultaneous therapy by previous injections of phenylbutazone;

FIG. 4: the course of the inflammation in dependability upon the time after artificial production of the inflammation by injection of Carrageenan with and without previous intraperitoneal injection of Fibrinogen;

FIGS. 5a, 5b 5c: The alteration of the whole Fibrinogen content (FIG. 5a) of the portion of coagulable Fibrinogen (FIG. 5b) and of circulating Fibrinogen (FIG. 5c) in dependability upon the time with and without injection of Carrageenan;

FIGS. 6a,6b 6c: the effect of the systematic application of the fibrinopeptides separated, with the help of the thrombin from fibrinogen or coagulated fibrins on rat paw oedema induced by Carrageenan.

The FIGS. 1a, b and 2 shows that, with rats, in the same way as with people, alterations in the plasma protein profile occur, specific to the illness. In order to show this connection, inflammations were artificially set up in rats; either Lipid-A intraperitoneally or Carrageenan sub-plantar was injected into a hind paw. The Lipid-A component of bacterial lipopolysaccharid-endotoxin was used, which was obtained from R 595 mutants of Salmonella Minnesota by known extraction methods, using phenol-chloroform-petroleum ether (Galanos, et al Eur. 1. Biochem. 9 (1969). 245–249; Risse et al., Eur. J. Biochem 1 (1967), 216–232).

Two mg of a suspension of 2 ml Lipid-A in sterile 0.9% saline solution were injected. The carrageenan used was a usual commercial product (Serva, Heidelberg) from which a 2% suspension in sterile 0.9% saline solution was made. 0.2 ml was injected. The animals were male Wistar rats (Gesellschaft für Strahlen und Umweltschutz, Neuherberg) with a weight of 90 to 140 g. After the corresponding spaces of time recorded in FIGS. 1 and 2, 3 rats were sacrificed at each test and the sera obtained from them pooled for evaluation. Only an 0.9% saline solution was injected into the animals of the control group.

Dependent upon the time, the alterations quoted in the Table 3, of the concentration of the administered plasma proteins were thus produced. The determination of the percentage alteration resulted, by a 2-dimensional immunoelectrophoresis according to Clarke & Freeman (Clin.Sci. 35 (1968), 403–413.

The immunoprecipitates assignable to the individual plasma proteins are thus determined by corresponding stainings and after the passing of time related on the climax phase percentually to the beginning, (referring to the carrying out of the measurements compare Abd-el-Fattah, Scherer, Ruhenstroth-Bauer, Journal of Molecular Medicine 1 (1976), 211–221).

From the FIGS. 1 and 2, the result of these tests can actually be seen for 12 plasma-proteins. So far as the individual plasma proteins have no customary specification, they were specified solely with the number of the climax phase related to them by the evaluation (so, e.g. No. 24, 15, 12).

Thus, specific for inflammation in regard to rats, and also for an inflammation caused by Lipid-A respectively by Carrageenan, specific plasma protein profiles are produced.

Thus the maximum values of the percentage increase or decrease of the 30 different plasma proteins for inflammations caused by Lipid-A and Carrageenan over the elapse of time of the tests are quoted in Table 1.

Table 1 shows that, with 17 plasma-proteins, an increase in the concentration is produced; 8 remain unaltered; with 6 plasma-proteins a decrease in the concentration was produced. From the periodic course of the alterations in the concentrations of the individual plasma proteins, specific variations are produced. The high quantitive variation in regard to coeruloplasmin and hexopexin is especially to be pointed out. The decrease of various plasma proteins according to FIGS. 1b and 2b in regard to rats injected with Carrageenan is, further, quicker than with those injected with Lipid-A.

The test described as follows should make clear how a conventional therapy works out on the plasma protein profile. Moreover the effect of phenylbutazone, an inflammation-arresting material, is examined with four groups of rats. The groups A1 and A2 received subcutaneous injection of Lipid-A, respectively Carrageenan in the hind paws, the group B received the same dose of Carrageenan, but one hour before received an injection of a determined quantity of phenylbutazone, the group C (control group) an injection of an 0.9% saline solution and the group D an injection of an 0.9% saline solution, but—as with Group B—previously a phenylbutazone injection. The phenylbutazone (with Group B and Group D) was injected subcutaneously in the area of the scapula with a dosage of 200 mg/kg body weight. This dosage is sufficient to exclude an oedema on the injected rat paw. From rats of each group which, after 24, 48, respectively 72 hours after the beginning of the experiment, were sacrificed, the serum from 9 rats respectively was pooled and analysed.

The result is quoted in Table 2. Table 2 quotes the percentage increase (+) or decrease (−) of the alterations in the concentrations of the plasma proteins in rat serum during the acute reaction phase. The results shown in Table 2 are graphically shown in FIGS. 3a, b. The amazing result of this test, on which the invention is based, is as follows:

Although, before injection with Lipid-A respectively Carrageenan, phenylbutazone was given in a dosage which was sufficient to decrease every observable oedema, it did not result—as was to be expected by the differential diagnostic significance of the plasma protein profile at the beginning—in a correspondingly smaller or hardly marked plasma protein profile, but much more an increase. Also the presentation according to FIGS. 3a, b makes significant that for actually determined inflammations by the therapy with phenylbutazone specifically, an increase of the determined plasma proteins occurred. In the case of an injection with Lipid-A, with a therapy with phenylbutazone, the greatest increase resulted with the plasma protein identified as No. 24; the next highest increase occurred with α-1-acid glycoprotein, respectively the plasma protein identified as No. 15. With an injection of Carrageenan and therapy with phenylbutazone, the greatest rise in haptoglobin resulted, the next with α-1-acid glycoprotein, respectively the plasma protein identified as No. 24.

This connection—the therapy leads, in spite of suppression of the inflammation, not only to the suppression but to the increase of the plasma proteins specific to the illness—leads now inversely to the posing of the question whether the addition of the plasma proteins to be taken for a specific inflammation is not directly a therapy. As is to be shown subsequently, this question is to be answered in the affirmative. Hence it follows: The plasma proteins display a protection system inherent in the body, which, through the therapeutics known up to now (in the test: phenylbutazone) is set in motion. These therapeutics thus do not themselves work directly, but much more as a release for a protective system inherent in the body, which is formed by plasma proteins specific to the illness, respectively generally, specifically for a pathogenic process. The plasma protein profile discussed in the beginning thus does not only supply the differential diagnoses, but, at the same time, the suitable medicamentation in the form of such plasma proteins, the increase of which, specific to the illness, is released.

The inference that the increase in the concentration of determined plasma proteins gives a protective system inherent in the body, which is increased by a therapy, e.g. with phenylbutazone, is further confirmed in that, in regard to therapy with such a medicament, an increase in the concentration of determined plasma proteins then also occurs, if no inflammation or any kind of inflammation-promoting stimulation is given. In order to confirm this inference, the following further tests were carried out. It is known, that, as a reaction to determined inflammations or the rate of growth of a tumour, the concentration of the fibrinogens contained in the blood plasma, thus, likewise, of a plasma protein, increases with an effect of increasing the BKS (blood corpuscle reduction) speed and the acceleration of the coagulation. It is thus here a question of an increase specific to the illness, of the concentration of a plasma protein as was demonstrated above as a reaction to a stimulation with Lipid-A or Carrageenan. If now the increase of a plasma protein occasioned by the illness, as discussed above, is the reaction of a protection system inherent in the body, so an injection of fibrinogen must also lead to a decrease in the result of a stimulation affecting the increase of the fibrinogen content. Such a test is described as follows:

Male Wistar rats with a weight of 100 g received injections with 15 mg rat fibrinogen (Manufacturer: Koch-Light Ltd., Colnbrook) which was dissolved in an isotonic saline solution of 0.1% EDTA. A half hour later a sub-plantar injection of 0.1 ml 2% Carrageenan in a sterile isotonic saline solution followed in one hind paw. The same inflammation irritation was also injected into a control group of rats, into which previously only an NaCl solution was injected.

FIG. 4 (each point corresponds to tests with 5 or 6 animals); therein the extent of the inflammation is plotted, in dependence upon the time after the injection of Carrageenan and, indeed, not only for the rats into which fibrinogen had previously been injected but also for those who previously received no fibrinogen injection. The extent of the inflammation was determined in the usual way by means of the weight increase of the stimulated paws. According to that there results a 20 to 28% decrease in the formation of oedema in regard to the animals previously injected with rat fibrinogen in comparison with the control group. That confirms the abovementioned conclusion that fibrinogen, a plasma protein, reduces the results (oedema) specific to such pathogenic processes which, on their side, lead to an increase of fibrinogen content in the blood. Worthy of mention in this connection is the fact that further, human fibrinogen does not have this effect with rats, that this effect with rats is much more evoked only by rat fibrinogen.

In other words: A plasma protein which increases the BKS (blood corpuscle reduction) speed, which has been claimed, up to now, diagnostically as an indication of an inflammation, leads, further than that, with increased presence, to the diminishing of the oedema caused by a stimulation. Thus it is demonstrated that a therapy of a pathological process can, in this way, result directly in the fact that such plasma protein, the growth of which above the normal state follows on directly by this means, e.g. is added by injection. As further information shows, the result is, moreover, that an increase in the BKS speed is a more or less unspecific result of a very much differentiated defense system inherent in the body and reacting specifically to the illness; that it is shown, during the acute reaction phase, as an alteration of the concentration of the plasma proteins determined, so that an increase of the same by direct administration of these plasma proteins is a specific therapy.

It is now known that the fibrinogen, as most plasma proteins, is synthesized in the liver, thus not around the point of stimulation. With a peritoneal fibrinogen injection (made into the abdominal cavity) an effect at the point of stimulation by a Lipid-A, respectively Carrageenan injection accordingly presupposes that a resorption and a transport takes place and, indeed, from the site of the injection of the fibrinogen (abdominal cavity) to the point of stimulation (paw) with Lipid-A respectively Carrageenan. The depositions of the fibrinogen must ensue from thereon. For evidence of this procedure, Rat fibrinogen by $125_1$ (Amersham Buchler, Braunschweig) is indicated in known ways.

Six rats were, as in the previous experiment, injected with 15 mg of this radioactive labelled rat fibrinogen. This quantity is approximately equal to the quantity of the whole fibrinogen content of a healthy rat weighing 110 g. After 30 minutes three rats were injected with Carrageenan; the remaining three rats formed the control group. From then on the following quantities were measured:

(a) the total quantity of the plasma fibrinogen of the rats;

(b) the quantity of the fibrinogen labelled $125_1$ circulating in the circulation; and (c) the coagulable fibrinogen labelled $125_1$.

This measurement is recorded in Table 4 and described in FIGS. 5a, b, c.

From Table 4 it is shown that the concentration of the circulating rat fibrinogen is not noticeably increased by the injected $125_1$ fibrinogen. The resorption of the fibrinogen labelled $125_1$ apparently takes place very slowly; it is, with the rats injected with Carrageenan and the rats of the control group, not markedly different.

Not more than 4% of the total labelled fibrinogen could be traced at any fixed point of time in the blood circulation. On the other hand, with the Carrageenan injected rats, a noticeable increase of the concentration of the fibrinogen results at the point of the stimulation, i.e. the paw. That leads to the conclusion that the fibrinogen is transferred by the circulation from the place of its injection to the place of the stimulation. For the body's own defence mechanism, this means a transfer from the point of synthesis—thus, of the liver—over the circulation to the point of stimulation.

This result leads to the following reflection: As the plasma protein specific to the illness are synthesized in the liver and transferred to the place of this stimulation, somehow the information that a stimulation has taken place must reach the liver so that this, from then on, can undertake an augmented synthesis of the plasma proteins specific to the stimulation, which are concerned. It is, therefore, to be further asked: of what type is the provision of this information.

The so-called LEM mediators have already been described in the literature (Leukozytic Endogenous Mediator—LEM; compare Kampschmidt et al., Proc. Soc. Biol. Med. 146 (1974) 904–907; Pekarek et al.. Proc. Soc. Exp. Med. 141 (1972), 1029–1031; Pekarek et al., Proc. Soc. Exp. Biol. Med. 141 (1972), 643–648). This leukocytic endogenous mediator can be described as a protein-analogous substance with a molecular weight of 10,000 to 30,000, which is obtained from leukocyte (compare Pekarek et al., Proc. Soc. Exp. Biol. Med. 138 (1971), 728). For that purpose rabbits received an intraperitoneal injection of sterile saline solution which contained 0.2% glycogen. After 14 hours the peritoneal leukocytes were obtained, twice washed with a saline solution and then incubated at 37° C. for two hours. The LEM which was given up by the stimulated polymorphonuclear leukoctyes (PMN) was received in cell-free condition after centrifugation. In order to remove the contaminating proteins with high molecular weight, the crude (LEM) solution was filtered through an Amicon XM-100 filter and finally concentrated by a pressure filtration with an Amicon PM-10 filter. This LEM preparation was intraperitoneally injected into healthy rats. The dosage was similarly measured out to that quantity of LEM which separates $4.5 \times 10^7$ PMN 12 hours after the full development of a plasma protein profile (it can be supposed that LEM is shown, not as an individual protein effective as a mediator, but a whole group of proteins with small molecular weight, which control the syntheses of various plasma proteins in the liver).

In order to determine the physiological significance of the LEM in the connection under discussion, all the white blood corpuscles of the test animals were broken down by a combined treatment with methotrexate (3 times daily i.p. injections of 2.5 mg/kg body weight) and a 400 R-exposure. As a result of this treatment, the granulocytes which give off the LEM factor were no longer existent; there was, therefore, also no longer a natural LEM present in the circulation of the test animals.

The rats, deprived in such a way of their granulocytes and their LEM, received a sub-plantar injection of Carrageenan in the hind paws. The immunoelectrophoretic analysis of the rat sera 24 hours after this stimulation showed that the acute phase reaction, thus the alteration in the plasma protein specific to the illness, discussed in the introduction, against the expectation on the basis of the results presented at the beginning, was clearly reduced. After 48 hours, however, a fully developed altered plasma protein profile corresponding to this illness condition according to expectation was shown. Thus there came about, through the previous breakdown of the granulocytes of LEM given off, an important delay in the body's own system response. Whereas LEM was injected, so there came about a normal system response by increase of the plasma proteins, also then, when no stimulant, e.g. Carrageenan had been injected. This confirms that the delayed system response to Carrageenan, in reality, is to be traced back to a lack of circulating granulocytes, respectively also to other cells of the leukocytary system.

It is known that LEM already, before the conversion of the plasma protein synthesis of the liver, brings about the increased flow of free amino acids from the serum into the liver, and an increased hepatic RNA-synthesis (Wannemacher et al., Fed. Proc. 33, 1523 (1974). It is further known that, under its influence, zinc and iron, multiplied by the liver, is received, the serum copper level, rises as a result of the multiplied synthesis of coeruloplasmin and, speeded from the bone marrow, neutrophilic granulocytes are discharged into the peripheral blood (Beisel W.R., Ann. Rev. Med 26, 9 (1975)). All these pathophysiological system reactions, inclusive of the acute PPP-alterations and of the fever caused by the "endogenous pyrogen", are characteristic body reactions as are to be noted in the beginning stages of acute infections or bacterial inflammatory processes. The physiological function of many plasma proteins, particularly of the acidic glycoprotein synthesized in great quantities during the occurrence of inflammation, is unknown. The increase of the synthesis of a range of suppressions of proteolytic enzymes in order to check the tissue-destructive effect of the lysosomalic enzyme activities set free by granulocytes at the site of the inflammation, such as acid and neutral proteosis, collagenase, and elastase, seems evident. This is certainly known, to some extent, but collated once again as follows:

| Plasma Protein | Function |
| --- | --- |
| Fibrinogen | Blood clotting, local oedema suppression |
| α-1-Antitrypsin | Suppression of proteolytic enzymes |
| Antichymotrypsin | Suppression of proteolytic enzymes |
| α-2-Macroglobulin | Suppression of proteolytic enzymes |
| $C_1$-Esterase-Inhibitor | Suppression of proteolytic enzymes |
| Complement C3 and C5 | Chemotaxis, opsonisation |
| Haptoglobin | Combination and conservation of haemoglobin |
| Haptoglobin-haemoglobin Complex | Stimulation of collagenbiosynthesis |
| Coeruloplasmin | Copper combination, oxidase |
| C-reactive protein | Activation of complement, phagocytosis acceleration |

Although the function of many proteins which are subsequently synthesized to acute inflammatory irritations which are very much augmented, is still unknown, the former findings lead to the conclusion that the synthesis of the proteins of the acute phase is a general control function of the liver which, then, is intended to check the tissue-destructive influence of the local inflammatory occurrence and to start the enzymatic processes for a repair of the tissue damage.

The results given up to now can thus be collated as follows: The body's own defence system can be strengthened in two ways and a pathogenic process which is characteristically marked by a specific change in the plasma protein profile can be diminished, namely:

(a) through injection of such plasma proteins which are available, strengthened specifically to the illness;

(b) by administration of the LEM causing the strengthened synthesis.

A medicament according to the invention for a defined pathological process which is shown as an alteration of the plasma protein profile is thus obtained in such a way that this alteration of the plasma protein profile is fixed and that the medicament as effective substance, contains such plasma protein as is specific to the illness, as the body's own defence reaction is present, increased, in the plasma protein profile. Practically, probably, not always *only* the plasma proteins are used which are of importance for a specific sickness, but a mixture of all the plasma proteins which are important for illnesses in general. It is, then, to be expected that the inflamed organ will seek out those plasma proteins which are necessary for the special situation. Alternative to this, the medicament contains, as an effective substance, the LEM which accelerates the build-up of the body's own defence. The invention is thus also applicable if the alteration in the concentration is specific for several plasma proteins for a pathological process, so that the body's own defence is assisted by a mixture of these substances.

It is subsequently further described in which ways one of the above-mentioned plasma proteins, namely fibrinogen, works. A starting point for further reflection in this direction is the fact that, as shown in Table 5 and in FIG. 6a, b and c, only a relatively small portion of, at the highest, approximately 4% of fibrinogen is available in the circulating blood and that only approximately one-third of the fibrinogen is clottable.

Before the conclusions to be drawn from this are explained, perhaps the tests which have produced this determination may be demonstrated briefly:

The fibrinogen was, as also in the case of the previously mentioned tests: with rats, marked with radioactive material. The radioiodination ensued either with $Na^{125}I$ or with $Na^{131}I$ (NEN Chemicals, Boston, Mass.), using the Lactoperoxidase method. The establishment of the radioactivity in tests of the rat serum and plasma was undertaken with the assistance of a Gamma counter (Searle 1195 Gamma Counting System, Des Plaines, 111)—The ability of the $^{125}I$-Fibrinogen to clot measured 78.8%. The unmarked fibrinogen was established quantitatively by radial immunodiffusion in agarose gel, which contained rabbit anti-body.

15 mg of radioactive-marked rat fibrinogen, which quantity amounted to approximately the total fibrinogen content of the plasma of a healthy 100 g rat, was i.p. injected into six rats. After 30 minutes, three rats were injected with Carrageenan, while the remaining three rats formed the control group. The blood tests from each group were pooled then, and the whole concentration of fibrinogen in the rat plasma, the portion of the $^{125}I$-Fibrinogen circulating in the bloodstream and its ability to clot during the experiment was determined. The results are recorded in Table 5.

The data already given in Table 3 shows that an increase in the dosage of an intraperitoneal injection of fibrinogen above the smallest experimentally used dose, does not lead to a further increase of the suppression of the swelling of the rat paw. Moreover, it is shown, as further result, that an intracardiac injection of a dose of 5 mg/rat is less effective than a corresponding i.p. injection.

Table 5, the results of which are shown graphically in FIG. 6a–c, now confirms these results. It shows, namely, that the concentration of the rat fibrinogen circulating in the blood stream by injection of radioactive-marked fibrinogen, thus of $^{125}I$ fibrinogen, is not significantly increased. It is shown much more (2nd line in Table 5, FIG. 6b) that also, in regard to an increase in the total concentration of fibrinogen in the rat plasma, the portion in the circulating blood does not go above 4%. That confirms that the result already given in the previous paragraph, with the aid of Table 3, that an increase of the dosage of the i.p. injected fibrinogen over a fixed value brings no more increase in the effectiveness in the suppression of inflammation. The animals of the control group did not differ much more from those to which an injection of Carrageeenan was dispensed for the stimulation of inflammation in a significant way regarding the resorption of the radioactive-marked fibrinogen. Further, these results from the fact that only one-third of the circulating radioactive-marked fibrinogen can be brought to precipitate by coagulation, that the larger portion of the radioactive-marked protein is already subjected, in one form or another, to a change, i.e. is exhausted, as only such fibrinogen can be brought to coagulate, with which the disintegration process has not begun.

On the other hand, the result, by the following test, is that, with rats whose hind paws have been stimulated inflammatorily by a Carrageenan injection, at the point of the injection, in comparison with unstimulated control groups, a noticeable accumulation of the i.p. injected radioactive-marked fibrinogen respectively its degradation product is found.

In order to be able to carry out the determination, over the bulk of the test animals (rats) the distribution of radioactive-marked fibrinogen, which had been injected i.p. was measured, and, indeed, not only in the case of an inflammation stimulated by Carrageenan in a hind paw, but also with control animals in absence of such a stimulation. The measurement was carried out with the aid of a known body-radioscanning apparatus (Gamma-Camera, Ohio, Nuclear ON 110, 40 W 03412 Hochenergie-Collimator, (High Energy Collimator), Slon/Ohio, U.S.A.). $^{131}$I marked fibrinogen was i.p. injected with a dosage of 15 mg. This corresponds to a total radioactivity of 0.35 mCi. 30 minutes later the right hind paw was injected with Carrageenan. The control animal was similarly treated; into this, however, a similar amount of sterile plysiological common salt solution was injected into the hind paw instead of the Carrageenan. After four hours a radioscanning of both rats was carried out. The result was that with the animal which had received the Carrageenan injection, there was, at the point of stimulation, a clear accumulation of the $^{131}$I marked fibrinogen, there was not, however, with the control animal.

This group of tests described up to now, can be collated thus, as follows:

(a) only a relatively small part (maximum 4%) of the radioactive-marked fibrinogen reached from the point of the injection (i.p.) into the bloodstream;

(b) a relatively larger part (approximately ⅔) of the fibrinogen existing in the circulating blood is no longer able to clot;

(c) at the point of an inflammation, there is likewise a clear easily observed concentration of radioactive-marked fibrinogen, respectively its degradation products present;

(d) the increase in a change in the concentration of the fibrinogen in the blood plasma in regard to a rat stimulated by an injection of Carrageenan follows on after a known time (see FIG. 2a compare there the relatively high value after 16 hours).

Observations of the relatively small portion of radioactive-marked fibrinogen in the bloodstream now leads one to suppose that the effectiveness of the fibrinogen is based on the fact that the effectiveness proceeds, not from the fibrinogen itself, but from the degradation products arising from the reaction with thrombin. As regards the reaction of fibrinogen with the thrombin present in the blood, in the first instance fibrin is produced. This reaction goes on in such a way that from the α-chain of the fibrinogen and from the β-chain of the fibrinogen, parts actually dissolve out. These parts are the fibrinopeptides A and B. They remain in solution, they can also be transported over the bloodstream to the point of a stimulation. Besides the fibrinopeptides which, according to quantity, form only by far the smaller part of the products of the reaction of fibrinogen and thrombin, fibrin is formed also. Although the monomer condition of these with this reaction remains preserved after the dissolution of the fibrinopeptides A and B from the α-chain, respectively from the β-chain, they crumble away and form an indissoluble clot. Notwithstanding, they carry as usual, the radioactive marking. That explains that an especially higher portion of the radioactive-marked material and, indeed, the fibrin occurring with this reaction remains lying thus at the point of the i.p. injection.

The tests shown subsequently now confirm that it is the fibrinopeptides A and B which cause the inflammation-suppressing effect.

In order to examine this, first of all fibrinogen was submitted to a degradation process in regard to which no fibrinopeptide was produced. For this purpose 3 mg of rat fibrinogen with 1 mg Cu-plasmin was incubated at 37° C. for 0, 10, 30 and 120 minutes time and subsequently injected in a dosage of, respectively, 5 mg/rat. The observation of the development of the oedema in the hind paw of a rat, four hours after stimulation by an injection of Carrageenan resulted, with none of the rats which were treated in such a way, in comparison to those rats injected with a sterile physiological common salt solution, in any suppression or reduction of the course of the inflammation. It can be concluded from this that fibrinogen digested with plasmin, respectively the degradation products arising therefrom, have no kind of effect.

In contrast to this, on the other hand, a clotting formation was brought about which corresponds to the course of the reaction of the fibrinogen with the body's own thrombin by formation of fibrin with a simultaneous splitting up of the fibrinopeptides A and B. For this purpose a clotting was induced in a solution of rat fibrinogen (5 ml fibrinogen/ml physiological common salt solution) by addition of thrombin and fresh rat serum (2 U thrombin+0.1 ml rat serum/ml fibrinogen solution). After the clot formation, it was centrifuged; the liquid left over from the clotting, which contains fibrinopeptides set free by the reaction with thrombin was then injected into the rats, cardially and also intraperitoneally. For the purpose of the intracardiac injection the solution was added to the fibrinopeptides, in addition heparin (0.7 U/rat). Instead of this solution, sterile physiological common salt solution with an equal quantity of thrombin and heparin was injected into the animals of the control group. Fibrinopeptides were injected into each rat of the test group in the quantity which was brought about with the corresponding reaction from a quantity of 5 mg fibrinogen. Moreover, the corresponding fibrin clot was mechanically homogenised and further rats injected.

The results of these experiments, which are shown in Table 6 confirm the suppositions. In principle, the same inflammation-suppressing effect occurs by suppression of the one measure for the swelling-up of the hind paw of the rat, showing the inflammation by the injection of fibrinopeptides, as has also occurred according to the older record, when fibrinogen, the initial product, is injected.

With intraperitoneal injection of fibrinopeptides, there occurs (line 3 in Table 6), in comparison with the animals of the control group, after four hours, a suppression of the swelling of the paw, of about 19.2%. With animals with which the fibrinopeptide was injected intracardially, there occurs, after two hours, a suppression of about 15.2%; after four hours, however, the effect is no longer evident. This distinction is thereupon well traced back in that the intraperitoneal injection leads to a certain storage effect.

In contrast to this, by application of the homogenised fibrin, there was a much smaller effect (Table 6, line 4).

These results demonstrate that it is directly the degradation products arising from the reaction of fibrinogen with thrombin which show the inflammation-suppressing effect. This reaction takes place in the body as the body itself contains thrombin-active systems. This supposition is also consistent to that of the test result after which, also, a certain inflammation-suppressing effect, if not also in the same dimension, was given by application of the remaining fibrin; it is clear from this that fibrinopeptides can still be contained in the clot.

The demonstration of radioactive-marked fibrinogen, thus not only the reaction process with thrombin-attributed fibrinogen at the site of the inflammation means that at least one part of the effective fibrinopeptides is formed first at the site of inflammation. That means again that also the degradation product forming the greater part, according to quantity, originates as a result of this reaction, namely the fibrin at the site of the inflammation through this reaction. That explains also the formation of fibrin network at the site of a wound which, as is known, shows a first reaction of the body's own defence system at the site of the stimulation. These fibrin fibres thus give simultaneously the remains of the reaction with which the fibrinopeptide is shown as the body's own defence, by reaction of the fibrinogen with the body's own thrombin.

The increased permeability of the blood vessels given as a product of a local inflammation thus brings about, first of all, a leakage of the plasma proteins (fibrinogen), following on which an activating of the clotting system and a deposition taking place outside the blood vessels, of the fibrins formed by this clotting. This, first of all, works to a certain degree, mechanically as haemostatic clotting suppression, and after that, it works in a known way as stroma for the development of capilliaries and thus the migration of fibroblasts at the site of the inflammation. Moreover, it occurs that the accumulating fibrinopeptides A and B accumulating, by way of comparison in small quantities, now, with this fibrin formation prevent, in the way demonstrated, the swelling in the train of the inflammation.

By a medicament which contains fibrinopeptide as effective substance, this effect is likewise brought about, respectively the body's own such effect is strengthened.

It has thus been laid down that the inflammation-suppressing effect of the fibrinogen originates from the degradation products, respectively cleavage products, which accumulate with the formation of fibrin with reaction of the fibrinogen with the thrombin present in the blood. It is these fibrinopeptides and, indeed, the fibrinopeptides A and B from which the inflammation-suppressing effect originates. They thus work, not only in the way that their separating-out from the chain of the amino acids which form the fibrinogen leads to a crumbling away of their monomers through which the fibrin originates, that through this a haemostatic suppression effect develops, rather can it be shown that a continuing automatic effect approaches the fibrinopeptides A and B which, through application of a fibrinopeptide as effective substance containing medicament, can be improved.

Table 1:

Maximum alteration in the concentration of 30 plasma proteins in the rat serum during the acute reaction phase after injection of Lipid-A, respectively Carrageenan

| Plasma Protein No. | Specification | Increase/decrease (in %) after the stimulation of inflammation with | |
|---|---|---|---|
| | | Lipid-A | Carrageenan |
| 1 | Pre-albumin | −58 | −52 |
| 2 | Albumin | −36 | −32 |
| 3 | | +39 | +34 |
| 4 | α-lipoprotein | unaltered | unaltered |
| 5 | α-1-macroglobulin | +33 | +15 |
| 6 | | unaltered | unaltered |
| 6a | | unaltered | unaltered |
| 7 | α-acid glycoprotein | +216 | +200 |
| 8 | | +15 | +25 |
| 9 | α-1-antitrypsin | +13 | +26 |
| 10 | Cholinesterase | −40 | −40 |
| 11 | Coeruloplasmin | +52 | +157 |
| 12 | | −38 | −37 |
| 13 | | unaltered | unaltered |
| 14 | | +26 | +15 |
| 15 | | +224 | +170 |
| 16 | | +11 | +25 |
| 17 | Haptoglobin | +37 | +88 |
| 18 | | +11 | +35 |
| 19 | | unaltered | unaltered |
| 20 | Hemopexin | +94 | +32 |
| 21 | | unaltered | unaltered |
| 22 | | +29 | +58 |
| 23 | $\beta_1$-A | +90 | +225 |
| 24 | | +121 | +175 |
| 25 | | +30 | +45 |
| 26 | Transferrin | −14 | −14 |
| 27 | $\beta_1$-C | −69 | −69 |
| 28 | β-Lipoprotein | unaltered | unaltered |
| 29 | | unaltered | unaltered |
| 30 | Ig G | +18 | +14 |

Table 2

Percentage increase brought about by Phenylbutazone (+) or reduction (−) in the alteration in the amount of 11 plasma proteins in the rat serum during the acute reaction phase.

| Serum-Protein | 24 hrs. after injection of | | 36 hrs. after injection of | | 48 hrs. after injection of | | 72 hrs. after injection of | |
|---|---|---|---|---|---|---|---|---|
| | Lipid-A | Carrageenan | Lipid-A | Carrageenan | Lipid-A | Carrageenan | Lipid-A | Carrageenan |
| α1-acid glycoprotein | +8 | +52 | +58 | +62 | +30 | +87 | +82 | +89 |
| Coeruloplasmin | +13 | −5 | +26 | +14 | ±0 | +68 | +13 | +55 |
| No. 15 | +10 | −36 | +48 | +24 | −4 | +75 | +42 | −12 |
| Haptoglobin | +5 | +29 | +28 | +76 | +11 | +87 | +16 | +70 |
| Hemopexin | ±0 | +19 | −13 | +38 | −13 | +56 | +26 | +31 |
| No. 24 | +48 | +33 | +81 | +55 | ±0 | +78 | +44 | +48 |

Table 2-continued

Percentage increase brought about by Phenylbutazone (+) or reduction (−) in the alteration in the amount of 11 plasma proteins in the rat serum during the acute reaction phase.

| Serum-Protein | 24 hrs. after injection of | | 36 hrs. after injection of | | 48 hrs. after injection of | | 72 hrs. after injection of | |
|---|---|---|---|---|---|---|---|---|
| | Lipid-A | Carrageenan | Lipid-A | Carrageenan | Lipid-A | Carrageenan | Lipid-A | Carrageenan |
| Pre-albumin | −6 | −13 | −12 | ±0 | −18 | −11 | −6 | −16 |
| Albumin | −4 | −11 | −15 | −16 | −11 | −18 | −1 | −23 |
| Cholinesterase | −5 | −16 | −2 | −12 | −17 | +5 | +7 | +11 |
| No. 12 | +26 | −4 | +10 | +9 | −19 | +4 | +2 | +11 |
| Transferrin | +6 | +5 | +2 | +3 | −6 | ±0 | −2 | ±0 |

Table 3

Effect of the systematic application of various quantities of rat fibrinogen on rat paw oedema caused through inflammation, 4 hours after a stimulation by Carrageenan injection.

| Type of Application | Quantity of injected Fibrinogen (mg) | Weight increase of the Paw (%)(+) | Reduction of the Swelling of the paw (%)(−) |
|---|---|---|---|
| Intraperitoneal injection | 6.25 | 30.75 ± 4.57 | 24.3 ± 11.2 |
| Intraperitoneal injection | 12.5 | 25.00 ± 11.14 | 38.4 ± 27.4 |
| Intraperitoneal injection | 25.0 | 33.00 ± 7.26 | 18.7 ± 17.8 |
| Intracardiac injection | 5.0 | 36.4 ± 8.17 | 10.3 ± 20.1 |
| Control Group | 0 | 40.6 ± 9.04 | 0 ± 22.2 |

(+) = standard deviation reckoned from the results of at least 4 individual rats.

Table 4:

| TIME after injections of $125_1$-Fibrinogen | Contents of $125_1$-marked Fibrinogen | | | | | | | | | |
|---|---|---|---|---|---|---|---|---|---|---|
| | 0 | | 1 hour | | 2 hours | | 6 hours | | 16 hours | |
| | Carrag. | Control Group | Carrag. | Control Group | Carrag. | Control Group | Carrag. | Control Group | Carrag. | Control Group |
| Total quantity of the rat plasma fibrinogen (mg/100 ml) | 270 | 300 | 255 | 310 | 325 | 290 | 340 | 310 | 710 | 340 |
| Portion (%) of the circulating $125_1$-marked fibrinogen | — | — | 1.6 | 1.35 | 3.95 | 2.74 | 3.13 | 3.16 | 2.2. | 1.5. |
| Portion (%) of the clottable fibrinogen | 78.8 | 78.8 | 19.3 | 35.6 | 46.9 | 39.5 | 38.3 | 28.4 | 43.3 | 35.1 |

Table 5:

Total concentration of fibrinogen and $125_1$ fibrinogen absorption in the circulating blood after intraperitoneal injection of $125_1$ fibrinogen in rats stimulated with Carrageenan and in control animals

| Time After injection of the $125_1$ fibrinogen | 0 | | 30 minutes | | 2 hours | | 6 hours | | 16 hours | |
|---|---|---|---|---|---|---|---|---|---|---|
| | Carr. | Cont: | Carr: | Cont: | Carr: | Cont: | Carr: | Cont: | Carr: | Cont: |
| Total concentration of the fibrinogen in the rat plasma (mg/100 ml) | 270 | 300 | 255 | 310 | 325 | 290 | 340 | 310 | 710 | 340 |
| Portion of the injected $125_1$ fibrinogen circulating in the blood % | — | — | 1.6 | 1.35 | 3.95 | 2.74 | 3.13 | 3.16 | 2.2 | 1.5 |
| Clottable portion of the $125_1$ fibrinogen (%) | 78.8 | 78.8 | 19.3 | 35.6 | 46.9 | 39.5 | 38.3 | 28.4 | 43.3 | 35.1 |

(+) = the total concentration of the fibrinogen in the plasma was determined with the help of radial immunodiffusion with rat fibrinogen - antiserum (Behringwerke AG, Marburg).

Table 6:

Effect of the systematic application of the separated-out fibrinopeptides with the help of thrombin, or clotted fibrin on the paw oedema of the rat induced with Carrageenan

| Treatment with | Application formation | Number of tested rats | Point of time of the fixing of the oedema after stimulation with Carrageenan Hours | Suppression of the swelling of the paw(+) % |
|---|---|---|---|---|
| Fibrinopeptide | i.c. | 12 | 2 | 15.2 ± 10.2 |
| Control animals | i.c. | 12 | 2 | 0 ± 8.4 |
| Fibrinopeptide | i.c. | 4 | 4 | −4.9 ± 9.9 |
| Control animals | i.c. | 4 | 4 | 0 ± 5.8 |
| Fibrinopeptide | i.p. | 15 | 4 | 19.2 ± 14.4 |
| Control animals | i.p. | 16 | 4 | 0 ± 10.4 |
| Fibrin | i.p. | 12 | 4 | 12.7 ± 11.4 |

Table 6:-continued

Effect of the systematic application of the separated-out fibrinopeptides with the help of thrombin, or clotted fibrin on the paw oedema of the rat induced with Carrageenan

| Treatment with | Application formation | Number of tested rats | Point of time of the fixing of the oedema after stimulation with Carrageenan Hours | Suppression of the swelling of the paw[+] % |
|---|---|---|---|---|
| Control animals | i.p. | 16 | 4 | 0 ± 10.4 | i.c. = intracardiac
i.p. = intraperitoneal
[+] = the percentage suppression is reckoned in relationship to the corresponding control animals.

What is claimed is:

1. A method of suppressing an inflammatory process in a mammal suffering from said process, wherein the inflammatory process is characterized in part by a higher than normal concentration of fibrinogen in the blood plasma of the suffering mammal, which comprises; administering to said mammal an effective amount of a blood plasma protein selected from the group consisting of fibrinogen, fibrinopeptide A and fibrinopeptide B.

2. The method of claim 1 wherein said administering is intravenously.

3. The method of claim 1 wherein said administering is intraperitonealy.

4. The method of claim 1 wherein said mammal is a human.

* * * * *